US006820025B2

(12) United States Patent
Bachmann et al.

(10) Patent No.: US 6,820,025 B2
(45) Date of Patent: Nov. 16, 2004

(54) METHOD AND APPARATUS FOR MOTION TRACKING OF AN ARTICULATED RIGID BODY

(75) Inventors: Eric R. Bachmann, Oxford, OH (US); Robert B. McGhee, Carmel, CA (US); Xiaoping Yun, Salinas, CA (US); Michael J. Zyda, Carmel, CA (US); Douglas L. McKinney, Prunedale, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/020,719

(22) Filed: Oct. 30, 2001

(65) Prior Publication Data

US 2002/0103610 A1 Aug. 1, 2002

Related U.S. Application Data

(60) Provisional application No. 60/246,215, filed on Oct. 30, 2000.

(51) Int. Cl.[7] .......................... G01C 17/38; A61B 5/103
(52) U.S. Cl. ........................................ 702/94; 600/595
(58) Field of Search ............................ 702/94, 151, 95, 702/150; 703/153; 600/595; 345/473

(56) References Cited

U.S. PATENT DOCUMENTS

| | | | | |
|---|---|---|---|---|
| 4,559,713 A | | 12/1985 | Ott et al. ........................ 33/302 |
| 5,645,077 A | * | 7/1997 | Foxlin .......................... 128/774 |
| 5,684,396 A | | 11/1997 | Aks et al. .............. 324/207.13 |
| 5,807,284 A | * | 9/1998 | Foxlin .......................... 600/595 |
| 5,953,683 A | * | 9/1999 | Hansen et al. ................ 702/95 |
| 6,148,280 A | * | 11/2000 | Kramer ....................... 703/153 |
| 6,163,021 A | | 12/2000 | Mickelson .................. 244/3.2 |
| 6,377,906 B1 | * | 4/2002 | Rowe .......................... 702/151 |
| 6,427,131 B1 | * | 7/2002 | McCall et al. .............. 702/150 |
| 6,428,490 B1 | * | 8/2002 | Kramer et al. .............. 600/595 |

OTHER PUBLICATIONS

"A Computer Simulation Study and Component Evaluation for a Quaternion Filter for Sourceless Tracking of Human Limb Segment Motion", Henault, Thesis, Mar. 1997.*

(List continued on next page.)

Primary Examiner—John Barlow
Assistant Examiner—Toan M. Le
(74) Attorney, Agent, or Firm—Donald E. Lincoln

(57) ABSTRACT

One embodiment the invention comprises a method of determining an orientation of a sensor. The method includes measuring a local magnetic field vector and a local gravity vector and using those measurements to determine the orientation of the sensor. Embodiments can include measuring the magnetic field vector and the local gravity vector using quaternion coordinates.

Another embodiment comprises measuring a local magnetic field vector, a local gravity vector, and the angular velocity of the sensor. These three vectors are processed to determine the orientation of the sensor. In one embodiment the three vectors can all be measured in quaternion coordinates.

Another method embodiment comprises determining a local gravity vector by providing a acceleration detector, moving the detector from a start point to an end point over a time period, and summing acceleration measurements over the time period. The local gravity vector is calculated using the summed acceleration measurements.

A system embodiment of the present invention includes a body having mounted thereon at least one sensor. The at least one sensor is configured to output orientation information to at least one processing unit that inputs the orientation information into a synthetic environment. The system also can include a display for displaying the orientation of the body with respect to the synthetic environment.

8 Claims, 6 Drawing Sheets

OTHER PUBLICATIONS

Kuipers, J., "Quaternions and Rotation Sequences", Princeton University Press, Inc. 1998.

McGhee, R., "Some Parameter–Optimization Techniques", Digital Computer User's Handbook, McGraw–Hill, pp. 234–253, 1967.

McGhee, R., et al., "Real–Time Tracking and Display of Human Limb Segment Motions Using Sourceless Sensors and a Quaternion–Based Filtering Algorithm—Part I: Theory," MOVES Academic Group Technical Report, NPS–MV–01–001, Naval Postgraduate School, Monterey, CA 2000.

McGhee, R., et al., "An Investigation of Alternative Algorithms for Singularity–Free Estimation of Rigid Body Orientation from Earth Gravity and Magnetic Field Measurements," Ph.D. dissertation, Naval Post Graduate School, Monterey, CA 2001.

Bachmann, E., "Inertial and Magnetic Angle Tracking of Limb Segments for Inserting Humans into Synthetic Environments", Ph.D. dissertation, Naval Postgraduate School, Monterey, CA 2000.

U.S. Provisional Patent Application No. 60/246,215, filed Oct. 30, 2000, entitled "Apparatus for real time tracking and display of the position and posture of a body using hybrid sourceless sensors, if positioning and a quaternion based complementary filtering algorithm".

International Search Report, PCT—ISA/US, mailed May 31, 2002.

* cited by examiner

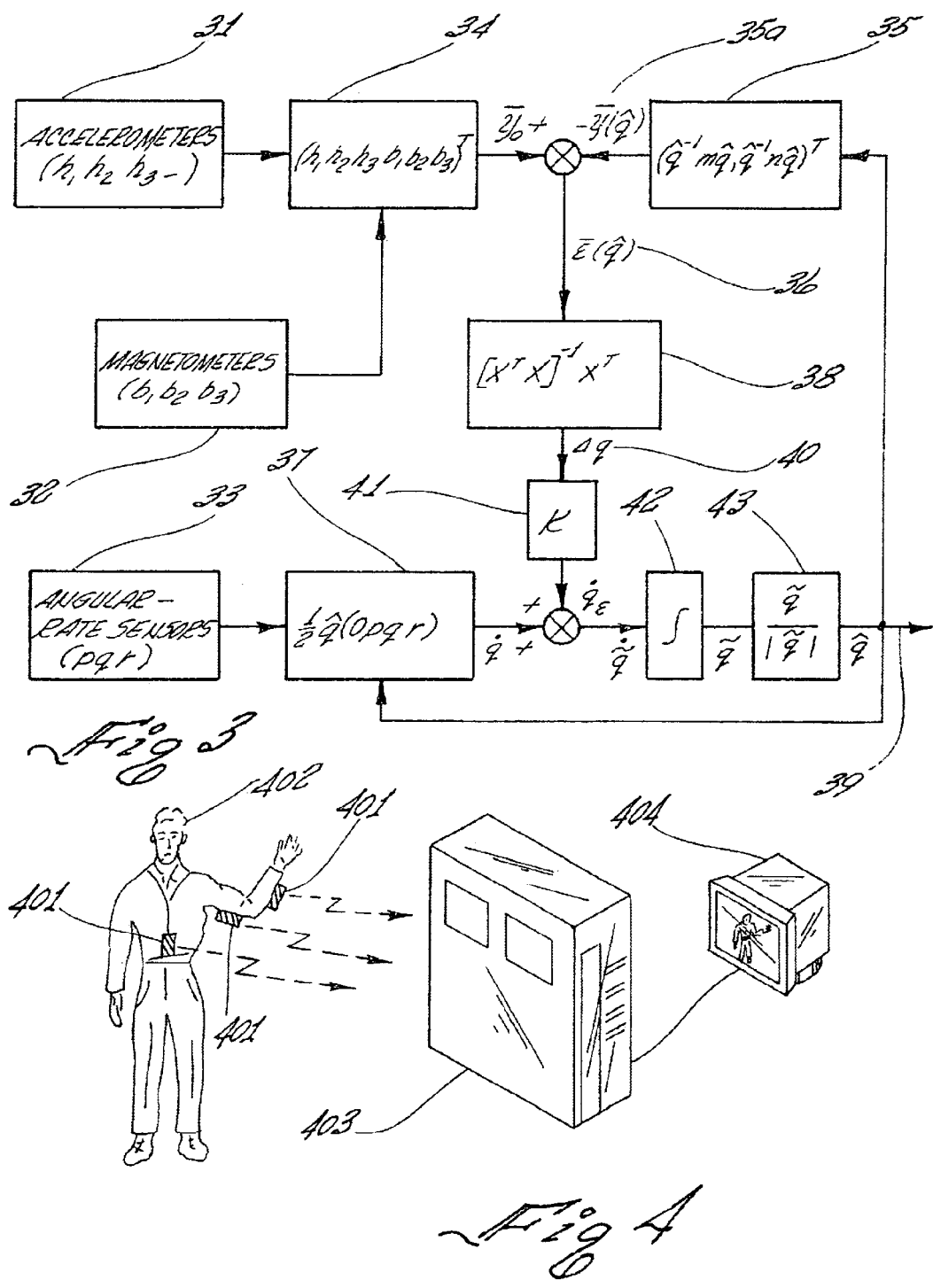

METHOD AND APPARATUS FOR MOTION TRACKING OF AN ARTICULATED RIGID BODY

RELATED APPLICATION

This application is related to, and claims priority from the U.S. Provisional Application Ser. No. 60/246,215, entitled "Apparatus for Real Time Tracking and Display of The Position and Posture of a Body using Hybrid Sourceless Sensors, RF Positioning, and a Quaternion Based Complementary Filtering Algorithm", filed on Oct. 30, 2000. This provisional application is hereby incorporated by reference in its entirety.

TECHNICAL FIELD

The invention described herein relates to methods and apparatus for tracking the orientation (also referred to herein as posture) of an object. More particularly, the invention relates to methods and apparatus for tracking the posture of an articulated rigid body. Still more particularly, the invention relates to methods and apparatus for tracking the posture of articulated rigid bodies using quaternion based attitude estimation filtering and displaying the posture of the body.

BACKGROUND

Embodiments of the present invention are directed towards methods and devices for tracking the orientation (posture) of human bodies. In particular such orientation information can be inserted into a synthetic (computer generated) environment where the motion of the tracked body can become part of the synthetic environment. Previous motion tracking systems of the type known in the art have a number of limitations that substantially limit their usefulness.

Currently available motion tracking technologies are limited by their reliance on a generated signal and/or the need to have the tracked body remain in sight of fixed stations positioned around a working volume. In either case there is a requirement to maintain some type of link over a distance. Regardless of the type of signal used, it can be generally referred to as a "source." Usually, the effective range over which the link may be maintained is limited. Moreover, data update rates may be limited by the physical characteristics of the source used. Additionally, interference with, or distortion of, the source can result in erroneous orientation measurements. If the link is broken, a complete loss of track will result.

One type of tracking system known in the art is the so-called mechanical tracking system. Such systems use an artificial exo-skeleton, which is worn by the user of a synthetic environment (typically, a computer-created simulated environment). Sensors (e.g., goniometers) within the skeletal linkages of the exo-skeleton have a general correspondence to the actual joints of the user. Joint angle data is fed into kinematic algorithms that are used to determine body posture and limb position. However, since the exo-skeleton is worn by the user, other systems must be used to ascertain the position of the user within the simulated environment. Such systems are fraught with numerous drawbacks. For one, aligning the goniometers with the joints of a human body is difficult, especially with multiple degree of freedom (DOF) joints. Additionally, the joints of the exo-skeleton cannot perfectly replicate the range of motion of the joints of a human body. Thus, such technologies can provide only a rough approximation of actual body movement. Another limitation stems from the fact that human bodies are of different sizes and dimensions. As a result, the exo-skeleton must be recalibrated for each user. Yet another limitation is imposed by the encumbrance of the exo-skeleton itself. The weight and awkward configuration of the exo-skeleton prevent a human user from interacting with his environment in a natural manner. As a result, it is unlikely that the user will become immersed in the synthetic environment in the desired manner.

Another widely used system is a magnetic tracking system. In such systems a large magnetic field is generated and calibrated. The user has many small sensors mounted at various points on his body. The sensors are sensitive to the generated magnetic field. Thus, changes in position and orientation of the users body with respect to the generated magnetic field can be detected by the magnetic sensors. Some of drawbacks of such systems include very short range and difficulty in calibrating the generated magnetic field. The short range stems from the fact that magnetic fields decrease in power inversely with the square of the distance from the generating source. This restricts the use of such systems to areas about the size of a small room. In order to use a larger working area, user movement must be modified or scaled in some manner. As a result, the magnitude and frequency of position and orientation errors increase rapidly. Additionally, the presence of ferromagnetic material (like the metal in belt buckles or weapons) distorts the generated magnetic fields. Additionally, the magnetic sensors pick up noise from other magnetic fields generated in or near the environment. Unfortunately, these distorting magnetic fields are commonplace, being easily generated by a plethora of devices, including computer monitors, fluorescent lighting, powered electrical wiring in the walls, as well as many other sources. Additionally, other sources of magnetic field error exist. Only with the aid of extremely detailed look-up tables can even moderately accurate measurements be obtained. Thus, magnetic tracking based on a generated magnetic field is subject to positional and orientation inaccuracies which are highly variable and unpredictable.

Another system for detecting position and orientation of a body uses so-called optical sensing. Optical sensing, in general, covers a large and varying collection of technologies. All of these technologies depend on the sensing of some type of light to provide position and orientation information. Consequently, all of these technologies are subject to inaccuracies whenever a required light path is blocked. Additionally, these technologies suffer from interference from other light sources. All of these optical sensing systems require specially prepared environments having the necessary emitters and sensors. This prevents widespread usage and presents a significant and expensive limitation.

Yet another approach is a tracking system using acoustic trackers. Like the previously described magnetic trackers, such systems are limited in range due to the inherent limitations of sound propagation. Additionally, the physics of sound limit accuracy, information update rate, and the overall range of an acoustic tracking system. Moreover, due to the relatively directional nature of sound, clear lines of sight must be maintained in order to obtain accurate readings. Additionally, due to the relatively slow speed of sound, there are latency problems with such acoustic sensor systems. As is evident from the foregoing discussion, conventional approaches for the tracking of body orientation have some serious limitations.

SUMMARY OF THE INVENTION

In accordance with the principles of the present invention, systems, method, and apparatus for body tracking is disclosed. A method embodiment for tracking the orientation of a sensor comprises measuring an angular velocity of the sensor to generate angular rate values which are integrating and normalizing to produce an estimate of sensor orientation. The method continues by measuring a local magnetic field vector and measuring local gravity vector and correcting the estimate of sensor orientation using the local magnetic field vector and local gravity vector.

Another method embodiment comprises measuring an angular velocity of the sensor to generate an angular rate quaternion, integrating and normalizing the angular rate quaternion to produce an estimated sensor orientation quaternion. The local magnetic field vector and local gravity vector are measured. A measurement vector is determined from the local magnetic field and local gravity vectors. A computed measurement vector is calculated from the estimated sensor orientation quaternion and comparing with the measurement vector to generate an error vector that defines a criterion function. The criterion function is minimized and an error estimate quaternion is output. The error estimate quaternion is integrated and normalized to produce a new estimated sensor orientation quaternion which can be output as a sensor orientation signal. The entire process is repeated except that the new estimated sensor orientation quaternion is used for calculating a computed measurement vector. The process continues until tracking is no longer desired.

Another method embodiment of tracking the orientation of a sensor comprises providing a starting estimate of sensor orientation, measuring the local magnetic field vector and measuring the local gravity vector. A measurement vector is determined from the local magnetic field vector and the local gravity vector. A computed measurement vector is calculated from the estimate of sensor orientation and compared to the measurement vector to generate an error vector that defines a criterion function. A Gauss-Newton iteration is performed, resulting in a minimized criterion function generating an error estimate that is integrated and normalized to produce a new estimate of sensor orientation. As with the forgoing embodiment, the entire process is repeated except that the new estimate of sensor orientation is used for calculating a computed measurement vector. The process continues until tracking is no longer desired.

Yet another method of tracking the orientation of a sensor comprises providing a starting estimate of sensor orientation quaternion measuring a local magnetic field vector and a local gravity vector and determining a measurement vector from the local magnetic field vector and the local gravity vector. A computed measurement vector is calculated from the estimate of sensor orientation, using quaternion mathematics.

The measurement vector is compared with the computed measurement vector to generate an 6×1 error vector that defines a criterion function and a mathematical operation is performed that results in the minimization of the criterion function and outputs a 4×1 quaternion error estimate. The quaternion error estimate is integrated and normalized to produce a new estimated sensor orientation quaternion. The entire process is repeated except that the new estimated sensor orientation quaternion is used for calculating a computed measurement vector. The process continues until tracking is no longer desired.

A method for determining a local gravity vector values comprises, moving the sensor from a start point to an end point over a time period; taking measurements of the total acceleration vector during the time period, time weighted summing the measurements of the acceleration vector over the time period, and calculating gravity vector values using the summed total acceleration measurements.

Embodiments of the invention also include sensor apparatus comprising a magnetic field detector configured to measure a magnetic field vector and output a local magnetic field vector signal and an acceleration detector configured to detect a local gravitational field vector and output a local gravitational field vector signal. A related embodiment further includes an angular velocity detector configured to detect an angular velocity vector of the sensor and output angular velocity signal.

Embodiments of the invention include a system for tracking the posture and orientation of body, the system comprising a body having mounted thereon at least one sensor, each sensor including a magnetometer for measuring a magnetic field vector and a acceleration detector for measuring a body acceleration vector, and at least one processor for receiving input from the magnetometer and acceleration detector and using said input to calculate a local magnetic field vector and a local gravity vector and to determine the orientation of the body. The processor of the system can be further configured to correct for offset between body coordinates and sensor coordinates. The system can further include a display for displaying the position and orientation of the body with respect to a synthetic environment. Further embodiments use sensors that include angular velocity detectors.

Other aspects and advantages of the invention will become apparent from the following detailed description and accompanying drawings which illustrate, by way of example, the principles of the invention.

BRIEF DESCRIPTION OF THE DRAWINGS

The following detailed description of the embodiments of the invention will be more readily understood in conjunction with the accompanying drawings, in which:

FIG. 3 is a simplified block diagram of a filtering method embodiment in accordance with the principles of the present invention FIG. 4 is a block diagram of a system embodiment of the present invention.

It is to be understood that in the drawings like reference numerals designate like structural elements.

DETAILED DESCRIPTION OF THE DRAWINGS

The embodiments of the present invention provide a method and apparatus for tracking the posture of a body without the need for a generated field (or source) or a plurality of fixed stations. Advances in the field of miniature sensors over the last decade make possible inertial/magnetic tracking of the orientation of tracked body in three dimensions. In particular such sensors can be used to track human body limb segments in three dimensions. In accordance with the principles of the present invention such tracking incorporates the passive measurement of physical quantities that are directly related to the rate of rotation and orientation of a rigid body. The "sourceless" nature of this technique makes possible full body posture tracking of multiple users over an area that is only limited by the range of a wireless LAN. Since orientation estimates are based only on passive measurements, nearly all latency in such a system is due to the computational demands of the data processing algorithms involved and not physical characteristics of the generated source.

Figures 1, 2A, 2B:
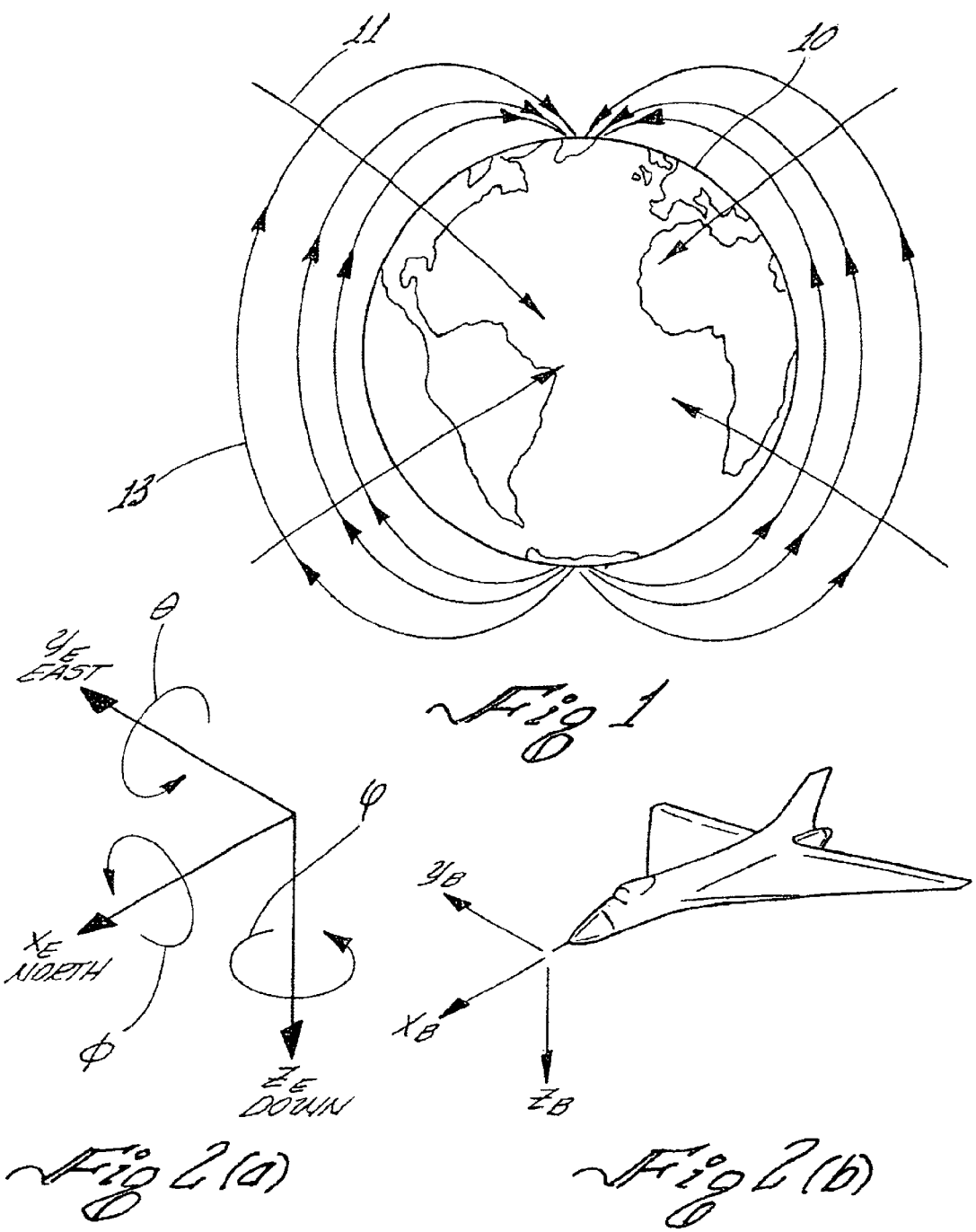
FIG. 1 is a figurative depiction of the earth's surface and its relationship with a example pair of a magnetic field vector and gravity vector.
FIGS. 2(a) and 2(b) depict reference and body coordinate systems respectively

An embodiment of the present invention makes use of the fact that a local magnetic field vector and local gravity vector can be defined. FIG. 1 is a simplified figurative illustration of the surface of the earth 10 showing a local gravity vectors 11 and a local magnetic field vector 13. In general, for any object positioned on the earth 10, the gravity vectors always points to the earth's center of mass, which may be defined as "down". This phenomenon is simply illustrated in FIG. 1. Additionally, the magnetic field vector 13 always points to magnetic north.

Sensor embodiments of the present invention, by tracking changes in the orientation of the sensor with respect to the local magnetic field vector and the local gravity vector, can detect changes in orientation of the sensor. An appropriately designed sensor can track the orientation of a body. Significantly, a system having a plurality of sensors, each mounted to a limb of an articulated rigid body can be used to track the orientation of each limb. In such systems, body posture can be tracked and introduced into a synthetic environment, thereby allowing a user to interface with the synthetic environment.

The Nature of the Mathematical Problem

A barrier to an effective implementation of effective body tracking systems stems from certain mathematical difficulties inherent in mapping body orientation from one coordinate system to another. These difficulties have presented problems which conventional approaches have not been able to resolve for over 100 years.

The nature of the problem is briefly outlined in the following paragraphs. A conventional way of describing the orientation of a rigid body uses "Euler angles" to describe the orientation of a rigid body in three dimensions. Euler angles describe the orientation of a rigid body using three rotations about specified axes. One commonly used reference coordinate system is the local "flat Earth" system. Such reference systems use an arbitrarily selected origin on the surface of the earth with respect to coordinate axes X, Y, and Z. By convention, the X-direction corresponds to local north, the Y-direction corresponds to local east, and the Z-direction corresponds to down as depicted in FIG. 2(a). Additionally, it is important to specify a body coordinate system which is attached to the body being tracked. FIG. 2(b) depicts such a system. This is also an X-Y-Z system with X pointing "out of the nose" in a positive direction, Y out the right side, and Z down. The subscript "E" designates earth reference coordinates ($X_E$, $Y_E$, $Z_E$) and the subscript "B" designates body reference coordinates ($X_B$, $Y_B$, $Z_B$). Euler angles represent the orientation of a rigid body using three rotations about specified axes in a specified order of rotation. For example, referring to FIG. 2(a), first rotation about the north axis, second rotation about the east axis, and third rotation about the down axis. These would be analogous to "roll", "elevation", and "azimuth". By convention, roll angle is designated by "$\Phi$", elevation by "$\theta$", and azimuth "$\psi$". It is to be noted that if the temporal order of rotations is reversed, body axis rotations yield exactly the same orientation as reference axis rotations.

The position of a point in space can be described using a three-dimensional point vector. A rigid body can be described in terms of a plurality of point vectors. An example vector can be represented by a vector V=[x y z]. In order to describe rotational behavior, matrix transforms are used. For example, if a vector is rotated about an angle $\Phi$ (e.g., about the $X_E$-axis described with respect to FIG. 2(a)), the following rotation transform can be used.

$$\begin{bmatrix} x' \\ y' \\ z' \end{bmatrix} = \begin{bmatrix} 1 & \ldots & 0 & \ldots & 0 \\ 0 & \ldots & \cos\varphi & \ldots & -\sin\varphi \\ 0 & \ldots & \sin\varphi & \ldots & \cos\varphi \end{bmatrix} \begin{bmatrix} x \\ y \\ z \end{bmatrix} = [rot(x, \varphi)] \begin{bmatrix} x \\ y \\ z \end{bmatrix}$$

Thus, the original x, y, z coordinates can be translated into the rotated coordinates x', y', z' through the application of a 3×3 rotation matrix. In the depicted example, the 3×3 matrix is designed to accomplish a rotation about the X-axis (represented by [rot(x, $\Phi$)]. Similar 3×3 rotation matrices exist for $\theta$ and $\Phi$ rotations about the Y- and Z-axis, respectively. Such rotation transforms are known to those having ordinary skill in the art and will not be described here in great detail. Additionally, a single 3×3 rotation matrix can be used to describe rotation about all three axes. One example of such a rotation matrix is shown below.

$$^E v = [rot(z, \psi)][rot(y, \theta)][rot(x, \varphi)]^B v = \begin{bmatrix} (\cos\psi\cos\theta) & \ldots & (\cos\psi\sin\theta\sin\varphi - \sin\psi\cos\varphi) & \ldots & (\cos\psi\sin\theta\cos\varphi + \sin\psi\sin\varphi) \\ (\sin\psi\cos\theta) & \ldots & (\sin\psi\cos\varphi + \sin\psi\sin\theta\sin\varphi) & \ldots & (\cos\psi\sin\varphi + \sin\psi\sin\theta\cos\varphi) \\ (-\sin) & \ldots & (\cos\theta\sin\varphi) & \ldots & (\cos\theta\cos\varphi) \end{bmatrix} ^B v = R^B v$$

As can be seen above, one of the difficulties inherent in using Euler angles and the aforementioned transform matrices is the sheer number of computations require to calculate each motion of a body. The problem becomes magnified as more and more bodies are simultaneously tracked. In the end, the complex calculations required using these existing algorithms require so much time that they can not effectively be used to track body position and orientation in real-time. This is a significant drawback.

In addition, Euler angle systems present certain computational difficulties. In particular is the problem of singularities. Singularities result when a sensor (or the rigid body to which it is attached) is tilted to a 90° (degree) angle. For example, if a rigid body is tilted such that it points straight up. At such a point, the roll and azimuth axes are co-linear. This results in a situation where neither the roll nor azimuth angles are uniquely defined, only their difference or sum can be specified uniquely. This problem becomes magnified when the time rate of change of Euler angles are used to quantify rates of angular rotation. This singularity problem is known to those having ordinary skill in the art and presents significant difficulty to conventional body tracking systems.

The principles of the present invention use magnetometer and accelerometer input subject to filtering to track body posture. In one implementation, Euler angles and their related coordinate transform matrices are used to calculate body orientation. Although computationally intensive, embodiments of the present invention can use Euler angle calculations to track body orientation. Additionally, angular velocity information can be used to correct for time lag errors. However, other embodiments of the present invention present a particularly advantageous approach for achieving body tracking using quaternion mathematics. Such embodiments eliminate the Euler angle singularity problem, and reduce the computational complexity of the invention.

In accordance with the principles of the present invention, sensor signals are input into an attitude estimation filter. Such a sensor can function using ordinary Euler angle mathematics. But, in preferred embodiment, the filter is a quaternion based complementary attitude estimation filter. Using quaternion mathematics results in an approximate 100-fold increase in processing efficiency. Although the present implementation is novel, the field of quaternion mathematics is known to those having ordinary skill in the art and is explained in detail in numerous mathematical texts. One example, is Kuipers, J, "Quaternions and Rotation Sequences", Princeton University Press, Inc., Princeton, N.J., 1998 (hereinafter "Kuipers"), which is hereby incorporated by reference.

Such a filter is used in conjunction with data supplied by sensors to produce a sensor orientation estimate expressed in quaternion form. In one embodiment, the sensors include a three-axis magnetometer and a three-axis accelerometer. In another sensor embodiment, the magnetometers and accelerometers are supplemented with angular rate detectors configured to detect the angular velocity of the sensor (comprising so-called Magnetic, Angular Rate, Gravity (MARG) sensors). Each MARG sensor contains angular rate detectors, accelerometers, and magnetometers. Estimation error is minimized using Gauss-Newton iteration. Unlike, other sensors known in the art, sensor embodiments of the invention can correct for drift continuously without any requirement for still periods.

In an articulated rigid body, posture is determined by estimating individual limb segment orientations through the attachment of sensors. The orientation estimates are used to animate a simple human model or avatar in real-time. The model directly accepts limb segment orientation information in quaternion form relative to a fixed reference frame (for example, an earth fixed reference frame). Simple calibration procedures are used to adjust sensor scale factors and null points, as well as account for offsets between the sensor coordinate frames and the frames associated with the limb segments to which they are attached.

Body Tracking Using Sensors with Magnetometers and Accelerometers

Referring to FIG. 3, q defines the variable for the orientation quaternion and q̂ defines values for the orientation quaternion. Accelerometers measure and return an approximation to the local gravity vector (the local vertical), the unit vector h 31. The magnetometers measure and return the direction of the local magnetic field vector (the unit vector b) 32.

In short, magnetometers can be used to measure the direction of the local magnetic field vector and accelerometers can be used to measure the direction of the local gravity vector. In one example, accelerometers 31 can be used to determine the local gravity vector by measuring the combination of forced linear acceleration and the reaction force due to gravity. As such accelerometer data can be used to determine a local gravity vector. That is because the accelerometer measures a total acceleration vector $\vec{a}_{measured}$ defined by $$\vec{a}_{measured} = \vec{a} + \vec{g} \quad (1)$$

In one embodiment, a three-axis accelerometer can be used to measure total acceleration (forced linear acceleration and gravitational reaction force) $\vec{a}_{measured}$ over a fixed time period. By conducting a time weighted summing (or integrating) of acceleration values over some relatively short time period the accelerations and decelerations exerted upon the body should average to zero. Time weighted summing methods emphasize the most recent measurements with respect to measurements taken in the past. Such methods are well known to those having ordinary skill in the art.

However, the effects of gravitational acceleration exerted on the body do not average to zero. Thus, components of the gravity vector can be determined. This works particularly well for objects (bodies) that undergo acceleration and deceleration on a relatively short time frame. For example, where a sensor is mounted on a forearm and is moved in normal course of motion. Determination of this local gravity vector allows the local vertical to be determined allowing correction of orientation relative to a vertical axis. Similarly, magnetometers 32 measure the local magnetic field in body coordinates. This information can be used to correct rate sensor drift errors in the horizontal plane. Thus, the vectors derived from accelerometer and magnetometer data comprise a method of determining orientation.

The magnetometer returns a local magnetic field vector (the unit vector b) in sensor coordinates. The accelerometer returns a local gravity vector (the unit vector h) in sensor coordinates. These two vector quantities b and h, expressed in sensor coordinates as pure vector quaternions, are unit vectors $$h=[0 \ h_1 \ h_2 \ h_3] \quad (2)$$

$$b=[0 \ b_1 \ b_2 \ b_3] \quad (3)$$

The vector parts from Eqns. (2) and (3) can be combined to produce a 6×1 measurement vector $y_0$ 34 in sensor coordinates:

$$y_o=[h_1 \ h_2 \ h_3 \ b_1 \ b_2 \ b_3]^T \quad (4)$$

In addition, it is known that gravity in earth coordinates is always down and can be expressed as the down unit vector in quaternion form as $$m=[0 \ 0 \ 0 \ 1] \quad (5)$$

Also, the local magnetic field in earth coordinates can be determined and normalized and can be expressed in quaternion form as $$n=[0 \ n_1 \ n_2 \ n_3] \quad (6)$$

As is known to those having ordinary skill in the art (e.g., See, Kuipers), Eqns. (5) and (6) can be mapped from the earth fixed frame to the sensor frame through quaternion multiplication (See, FIG. 3, Block 35) by $$h=q^{-1}mq \ \ b=q^{-1}nq \quad (7)$$

Combining the vector parts of Eq. (7) yields a single 6×1 computed measurement vector $\vec{y}(\hat{q})$ 35a, wherein:

$$y(\hat{q})=[h_1 \ h_2 \ h_3 \ b_1 \ b_2 \ b_3]^T \quad (8)$$

and wherein the values for $h_1, h_2, h_3, b_1, b_2, b_3$ are generated by mapping m and n through as an estimated orientation quaternion.

Then the difference between the actual measurements $y_0$ and the computed measurement vector is defined as the error vector $\vec{\epsilon}(q)$ 36

$$\vec{\epsilon}(q)=\vec{y}_o-\vec{y}(\hat{q}) \quad (9)$$

In viewing Eqn. 9, it is noted that if in Eqn. 8 there is no measurement noise, the minimum difference between the measured and computed values will equal the zero vector.

The square of the error vector (Eq. 9) is termed the criterion function $$\Phi(q)=\vec{\epsilon}^T(q)\vec{\epsilon}(q) \quad (10)$$

The criterion function is a scalar which can be minimized 38 (also referred to herein as criterion function minimization by filtering). In one filter embodiment, the error vector is minimized by minimized the criterion function using Gauss-Newton iteration. The details of a Gauss-Newton iteration are known to those having ordinary skill in the art. One example of such an implementation is described in McGhee, R., "Some Parameter-Optimization Techniques," Digital Computer User's Handbook, McGraw-Hill, pp. 234–253, 1967, (hereinafter "Handbook") hereby incorporated by reference. This method is based on linearized least squares regression analysis where $\vec{y}_0$ is considered a vector of data points and $\vec{y}(q)$ is a vector to be fitted to those points. The forgoing filter can be implemented using sensors having magnetometers 31 and accelerometers 32. Alternatively, other filtering embodiments can be employed including, but not limited to least squares filtering, Wiener filters, Kalman filters can be used. Such sensor and filter systems provide suitable method and apparatus for determining orientation (posture) of rigid bodies and articulated rigid bodies. The output of the filters can be integrated 42 and normalized 43 to provide an estimated orientation quaternion 39. However, due to magnetometer 31 and accelerometer 32 measurement inaccuracies, sensor drift error, and time lag present in such filtering systems improvements can be in the accuracy of such a system.

Body Tracking Using MARG Sensors

The accuracy of such method and system embodiments can be enhanced by using sensor angular velocity data supplied by an angular rate detector. FIG. 3 depicts the inputs from sensor embodiments that include angular velocity (rate) detectors 33. Interpreted in this way, such a filtering embodiment measures angular rate information 33, and uses measurements of local magnetic field 32 and local gravity 31 to correct the angular rate information or integrated angular rate information.

The angular rate detectors 33 provide angular rate information 37 to the filtering system. Thus, as with the previously discussed embodiment, accelerometers return an approximation to the local gravity vector h 31 and the magnetometers return the direction of the local magnetic field vector b 32. Again, a 6×1 measurement vector $y_0$ 34 in sensor coordinates is produced (Eqn. (4)). Again, in accordance with Eq. (7), Eq. (5), and Eq. (6) are approximations mapped from the earth fixed frame to the body frame through quaternion multiplication 35. And a 6×1 computed measurement vector $\vec{y}(\hat{q})$ 35a is generated. As previously described, the difference between the measurement vector $y_0$ and the computed measurement vector $\vec{y}(\hat{q})$ is the error vector $\vec{\epsilon}(q)$ 36 and the square of the filter modeling error is termed the criterion function. The error vector is then minimized. For example, using Gauss-Newton iteration.

In such an embodiment the filter inputs are from a three-axis accelerometer ($h_1, h_2, h_3$) 31, a three-axis magnetometer ($b_1, b_2, b_3$) 32, and a three-axis angular rate sensor (p, q, r) 33. Its output is a quaternion representation of the orientation of the tracked object q̂ 39.

In this embodiment, such magnetometer and accelerometer data (32, 31, respectively) can be considered complementary to sensor angular rate 33 data. Such angular rate data 33 can be used to describe sensor orientation. If the input from the angular rate sensor 33 were perfect (i.e., accurate, noiseless, and unbiased) it could be directly processed to obtain a rate quaternion $$\dot{q} = \frac{1}{2} q \otimes (0, p, q, r) = \frac{1}{2} q^s \omega \quad (11)$$

where q is a quaternion representing the current orientation, the indicated product is a quaternion product and the superscript S means measured in the sensor reference frame.

Single integration 42 of $\dot{q}$ is normalized 43 to produce a quaternion $\tilde{q}$, which describes new value for estimated orientation of the sensor prior to normalization 43. However, in normal operating environment, the output 33 of angular rate detectors tends to drift over time. Thus, rate detector data 33 can be used to determine orientation only for relatively short periods of time unless this orientation is continuously corrected using "complementary" data from additional sensors (here, accelerometer 31 and magnetometer 32). Thus, as previously explained with respect to Eqns (9) and (10) a Gauss-Newton iteration 38 is performed to correct a measured rate quaternion (See, FIG. 3, 36).

A full correction $\Delta q_{full}$ 40, if applied to the measured rate quaternion, can be defined by $$\Delta q_{full} = [X^T X]^{-1} X^T \epsilon(\hat{q}) = S^{-1} X^T \epsilon(\hat{q}) \quad (12)$$

where q̂ is the previous estimate for q and the X matrix is defined as $$X_{ij} = \left[ \frac{\partial y_i}{\partial q_j} \right] \quad (13)$$

Such an X matrix is described in great detail in McGhee, R., Bachmann, E., Yun X. & Zyda, M. "Real-Time Tracking and Display of Human Limb Segment Motions Using Sourceless Sensors and a Quaternion-Based Filtering Algorithm—Part I: Theory," MOVES Academic Group Technical Report NPS-MV-01-001, Naval Postgraduate School, Monterey, Calif. 2000 (Hereinafter, the Theory Paper) which is hereby incorporated by reference in its entirety.

Eq. (12) treats m and n as if they are perfect measurements of gravity and the local magnetic field. In reality, such data is frequently corrupted by noise. This can be corrected (41 FIG. 3) by using a scalar multiplier as defined by $$\Delta q_{partial} = a [X^T X]^{-1} X^T \vec{\epsilon}(\hat{q}) \quad (14)$$

where $$a = k \Delta t \quad (15)$$

and k represents the filter gain value 41. Thus, for discrete time step integration, the next estimate of sensor orientation would be $$\hat{q}_{n+1} = \hat{q}_n + \frac{1}{2} \hat{q}^B \omega \Delta t + a[X^T X]^{-1} X^T \epsilon(\hat{q}_n) \quad (16)$$

$$= \hat{q}_n + k \Delta t \Delta q_{full} + \dot{q}_{measured} \Delta t$$

Thus, such filtering systems can be thought of as time weighted filtering systems, because newer measurements are weighted more heavily than measurements taken more distant in the past.

Reduced Order Filtering

If q̂ is not constrained to unit length as depicted in FIG. 3, a unique solution to the optimization problem no longer exists and the X matrix will not be of full rank. In this case the regression matrix $$S = X^T X \quad (7)$$

will be singular and can not be inverted.

A more efficient alternative to the computation of $\Delta \hat{q}$ results from noting that if $$\hat{q}_{new} = \hat{q}_{old} + \Delta q_{full} \quad (18)$$

and if both $\hat{q}_{new}$ and $\hat{q}_{old}$ are unit quaternions, then any small $\Delta q_{full}$ must be orthogonal to q̂. That is, the only way to alter a unit vector while maintaining unit length is to rotate it, and for small rotations $\Delta q$ must be tangent to the unit four-dimensional sphere defined by $$q \otimes q^* = |q|^2 = 1 \quad (19)$$

where q* is the conjugate of q (See, previously incorporated reference by Kuipers). From the Orthogonal Quaternion Theorem (See, the previously referenced Theory Paper), if p and q are any two quaternions, then p is orthogonal to q if, and only if, p is the quaternion product of q and a unique vector v (real part equal to zero) where v is given by $$v = q^{-1} \otimes p \quad (20)$$

Accordingly $\Delta q$ can be written in the form $$\Delta q = q \otimes v = q \otimes (0 \ v_1 \ v_2 \ v_3) \quad (21)$$

With this constraint, linearization of the computed measurement vector, y(q), in FIG. 3, yields $$y(q + \Delta q) = y(q) + X \Delta q = y(q) + X(q \otimes (0 \ v_1 \ v_2 \ V_3))^T \quad (22)$$

and consequently:

$$\frac{\partial y}{\partial v_1} = X(q \otimes (0 \ 1 \ 0 \ 0)) = X(q \otimes i)^T \quad (23)$$

$$\frac{\partial y}{\partial v_2} = X(q \otimes (0 \ 0 \ 1 \ 0)) = X(q \otimes j)^T \quad (24)$$

and $$\frac{\partial y}{\partial v_3} = X(q \otimes (0 \ 0 \ 0 \ 1)) = X(q \otimes k)^T \quad (25)$$

Thus, when Gauss-Newton iteration is applied to unit quaternions, it is sufficient to solve for only three unknowns rather than four as in the methods for estimation of $\Delta q_{full}$ in Eq. (12). That is, if x is the 6×3 matrix $$X_v = \left[\frac{\partial y}{\partial v_1} \middle| \frac{\partial y}{\partial v_2} \middle| \frac{\partial y}{\partial v_3}\right] \quad (26)$$

then, $$\Delta v_{full} = [X_v^T X_v]^{-1} X_v^T \vec{\epsilon}(\hat{q}) \quad (27)$$

and $$\Delta q_{full} = \hat{q} \otimes (0, \Delta v_{full}) \quad (28)$$

Incorporation of the above into the Gauss-Newton algorithm, notably simplifies the computation of the $\Phi q$ quaternion since it requires only a 3×3 matrix inversion rather than the 4×4 matrix inversion of the basic algorithm. As is known to those having ordinary skill in the art, this is relevant since best algorithms for matrix inversion are of $O(n^3)$ complexity.

In an alternative approach, a reduced order X matrix (See, e.g., 38 FIG. 3 or Eq. 12) can be implemented. Such a matrix can be described as:

$$X = 2 \begin{bmatrix} 0 & -y_3 & y_2 \\ y_3 & 0 & -y_1 \\ -y_2 & y_1 & 0 \\ 0 & -y_6 & y_5 \\ y_6 & 0 & -y_4 \\ -y_5 & y_4 & 0 \end{bmatrix} \quad (29)$$

The derivation of this matrix is explained in R. B. McGhee, Bachmann, E. R. X. P. Yun, and M. J. Zyda, "An Investigation of Alternative Algorithms for Singularity-Free Estimation of Rigid Body Orientation from Earth Gravity and Magnetic Field Measurements", Ph.D. dissertation, Naval Postgraduate School, Monterey, Calif., 2001, which is hereby incorporated by reference. The $y_x$ values are the y values computed for the computed measurement vector $\vec{y}(\hat{q})$. In addition, the $y_x$ values can be calculated from any set of measured magnetic field vector values and gravity vector values in sensor coordinates. Such sets can be randomly determined or in accordance with some predetermined value. Also, the measured values of the magnetic field vector and gravity vector can be used to generate computed measurement vector $\vec{y}(\hat{q})$ and those y values can be input into the X matrix of Eqn. 29.

Weighted Least Squares Regression

With reference to FIG. 3 (at 36), detector data can be weighted putting greater or less reliance data received from the detectors 31, 32, 33. For example, greater or less reliance may be placed on magnetometer data 32 in comparison to accelerometer data 31. This could come about because one or the other of these signals could prove to be less accurate (or noisier) than the other. This can be achieved by merely redefining the error vector, $\epsilon$, as:

$$\epsilon(q) = \begin{bmatrix} y_{0_1} - y(q)_1 \\ y_{0_2} - y(q)_2 \\ y_{0_3} - y(q)_3 \\ \rho(y_{0_4} - y(q)_4) \\ \rho(y_{0_5} - y(q)_5) \\ \rho(y_{0_6} - y(\hat{q})_6) \end{bmatrix} \quad (30)$$

In such an embodiment, setting $\rho>1$ emphasizes magnetometer data, while $0<\rho<1$ puts greater weight on accelerometer data. This change alters the X matrix by multiplying the last three elements of each column by $\rho^2$. If a detailed statistical model is available for magnetometer and accelerometer errors for a particular experimental setting then, at least conceptually, the best value for $\rho$ could be obtained from linear estimation theory. In the absence of such statistical data, it is probably more productive to think of $\rho$ as a "tunable" parameter adjusted by "a best guess approximation optimization" in a given situation.

FIG. 4 shows one embodiment of an overall system implementation in accordance with the principles of the present invention. In the depicted embodiment three sensors are used to track the posture of a human body. Embodiments using fewer or greater numbers of sensors can be used. Typically, one sensor is attached to each limb segment to be tracked. The exact number of sensors used depends upon the degree of detail (resolution) desired by the user of such motion tracking devices.

By mounting a plurality of sensors on a body, the posture of the body can be determined and tracked. Sensors constructed in accordance with the principles of the present invention can be used to track motion and orientation of simple rigid bodies as long as they are made of non-magnetic materials. Examples include, but are not limited to hand-held devices, swords, pistols, or simulated weapons. However, the inventors contemplate using the principles of the present invention to track the posture of articulated rigid objects, in one example, human bodies. Such articulated rigid bodies feature a plurality of segments interconnected by a plurality of joints. Each of the segments can correspond to, for example, limbs and extremities such as head, hands, forearms, legs, feet, portions of the torso, and so on. The joints corresponding to wrist, elbow, shoulder, neck, backbone, pelvis, knees, ankles, and so on. The inventors contemplate the application of these principles to other articulated rigid body embodiments. For example, non-magnetic prosthetic devices, robot arms, or other machinery can by tracked in accordance with the principles of the present invention. Additionally, animal body motion can be tracked using such devices.

FIG. 4 is a figurative diagram of an overall system embodiment capable of detecting and tracking and orientation and posture of a rigid articulated body 402. One or more sensors 401 are positioned on a rigid articulated body 402. Such sensors 401 detect the posture of the articulated rigid body 402. This sensor information is output to a processing unit 403 (for example, a microprocessor configured as a central processing unit (CPU) of a computer) that calculates the posture of the articulated rigid body 402. This information can be transmitted from the sensors 401 to the CPU 403 using wires connected to the CPU 403 through appropriate interface circuitry. Such circuitry can include interface card, and if necessary I/O connection boards, and A/D cards. Alternatively, the sensor information can be transmitted to the CPU using wireless communication devices. In some embodiments, the sensors can include microprocessors that can accomplish much of the function of the interface circuitry or the posture calculation. Moreover, the CPU 403 can be incorporated into a small unit which can be carried on the body 402. Also, alternatively sensor information can be transmitted to a body mounted unit that then transmits the sensor information to the CPU 403 using, for example, wireless communication.

The CPU 403 then calculates the body posture and outputs a display signal to a display 404 (for example virtual reality display goggles or more conventional display devices such as monitors), thereby enabling the movement of the articulated rigid body 402 to be incorporated into a synthetic or virtual environment and then displayed. Where the movement being tracked is that of a non-magnetic simple rigid body (e.g., a simulated rifle or some like implement) the system is simplified, perhaps requiring only a single sensor 401 to track the motion of the rifle.

Sensor embodiments capable of incorporating the above-described principles can include a magnetic field detector and a gravitational field detector. In some embodiments micro-electro-mechanical system (MEMS) technology can be used to construct suitable devices. Other embodiments further include angular rate sensors.

One example of a suitable sensor device is an analog MARG sensor. In one embodiment such a sensor measures 10.1×5.5×2.5 cm. The analog output of the sensor is connected to a breakout header via a thin VGA monitor cable. Output range is 0–5 vdc. The power requirement of the sensors is 12 vdc at approximately 50 milliamperes. The primary sensing components are a triaxial accelerometer (e.g. a Model No. CXL04M3 manufactured by Crossbow, Inc.), a 3-axis magnetometer (e.g., Model No. HMC2003 from Honeywell), and three miniature angular rate detectors mounted in an orthogonal configuration (e.g., Tokin CG-16D series sensors available from Tokin American, Inc.). The individual components can be integrated using a single integrated circuit board with the accelerometers mounted separately. Rate sensor output voltage is amplified by a factor of five and filtered to attenuate rate sensor oscillator noise. Such MARG sensors can be obtained from McKinney Technology of Prunedale, Calif. Software or hardware biasing can be used to successfully integrate the signal from the angular rate detectors with the rest of the system. In one embodiment the angular rate signal can be passed through conditioning circuitry using capacitive coupling.

In order for the system to operate properly, the MARG sensors must be calibrated prior to posture tracking. Advantageously, unless the characteristics of the sensors themselves change, calibration need only be accomplished once. However, due to variations in the direction of the local magnetic field vector, better performance is to be expected if the direction of this reference is determined before each tracking session.

Accelerometers can be calibrated by placing them in a vertical position to sense gravity in one direction and then turning it over to sense gravity in the other. Halfway between the readings taken is the null point.

$$\text{accel null} = \frac{\text{accel max} + \text{accel min}}{2} \quad (31)$$

Multiplication of a correct scale factor times the accelerometer output values will result in a product of 1 g in one direction and −1 g in the other. This scale factor can be found using $$\text{accel scale} = \frac{(\text{accel units}) \times 2}{\text{accel max} - \text{accel min}} \quad (32)$$

A method of magnetometer calibration is very similar to that used for accelerometers. Instead of orienting each sensor relative to the gravity vector, each magnetometer is positioned to sense the maximum strength of the local magnetic field along both its negative and positive axes.

Determination of the null point of an angular rate detector is achieved by measuring the output of a static angular rate detector, then averaging the readings. Scale factors are then estimated by integrating the output of angular rate detector as it is subjected to a known angle of rotation. The scale factor for a rate detector can then be determined following a known rotation using $$\text{scale factor} = \frac{\text{known rotation}}{\text{estimated rotation}} \quad (33)$$

where the estimated rotation term is the result of integrating the output of the detector with a scale factor of unity.

The forgoing method can calibrate a MARG sensor using a level platform and a simple compass to indicate the direction of the local magnetic field. Each sensor can be calibrated by placing it in six positions allowing each accelerometer to sense gravitation acceleration in both the positive and negative directions, subjecting each rate detector to one or more known rotations and rotating the MARG sensor in a manner such that maximum and minimum local magnetic field readings could be obtained for each magnetometer.

The vertices of an individual segment of a human model can be described relative to a coordinate system having a z-axis in a down direction (for example, as shown in FIG. 2(*a*)) that is attached to the inboard (proximal) end of the segment. Such systems are known to those having ordinary skill in the art. See, for example, Bachmann, E., "Inertial and Magnetic Angle Tracking of Limb Segments for Inserting Humans into Synthetic Environments", Ph.D. dissertation, Naval Postgraduate School, Monterey, Calif., 2000, which is hereby incorporated by reference.

By aligning the coordinate axes of a sensor and a limb segment, the orientation of an individual limb segment can be set by applying to each vertex, v, the quaternion rotation $$q_{sensor} pullout; zu188100.900 v pullout; zu188100.900 q*sensor \quad (34)$$

where the unit quaternion $q_{sensor}$ is the estimated orientation produced by the filter processing the sensor output.

Misalignment between the sensor and limb segment axes can be taken into account by performing an additional fixed rotation using an offset quaternion $$q_{sensor} \otimes (q_{offsetpullout;zu188100.900vpullout;zu188100.900q*offset}) \otimes q^*_{sensor} \quad (35)$$

to each vertex, where $q_{offset}$ is the offset quaternion for the limb of the vertex.

When the human model is in the reference position, the limb segment coordinate axes are aligned with the corresponding Earth-fixed axes. That is the x-axis for each limb segment points toward the local north, the y-axis points east and the z-axis points down. The offset quaternion for each limb segment can be derived by noting that while the user is in the reference position the equation $$v = q_{sensor} \otimes q_{offset} \otimes v \otimes q^*_{offset} \otimes q^*_{sensor} \quad (36)$$

holds true.

Compensation for the way in which all sensors are attached to the limbs of a tracked subject can be accomplished by simply setting $q_{offset}$ for each limb segment to the inverse of the associated $q_{sensor}$ while the subject to be tracked is standing in a predetermined reference position.

To set the position of an individual limb segment, it is necessary to find a vector that describes the location of the inboard end of the limb segment. Once this vector is found, the final position of each vertex can be calculated through addition of this vector to the rotated coordinates of each vertex. Thus, the final position of a limb segment vertex is given by $$p_{trans} + q_{sensor} \otimes (q_{offset} \otimes v \otimes q^*_{offset}) \otimes q^*_{sensor} \quad (37)$$

where $p_{trans}$ is the vector sum of rotated translation vectors associated with limb segments that are between the body origin and the limb segment being positioned.

Figure 5A:
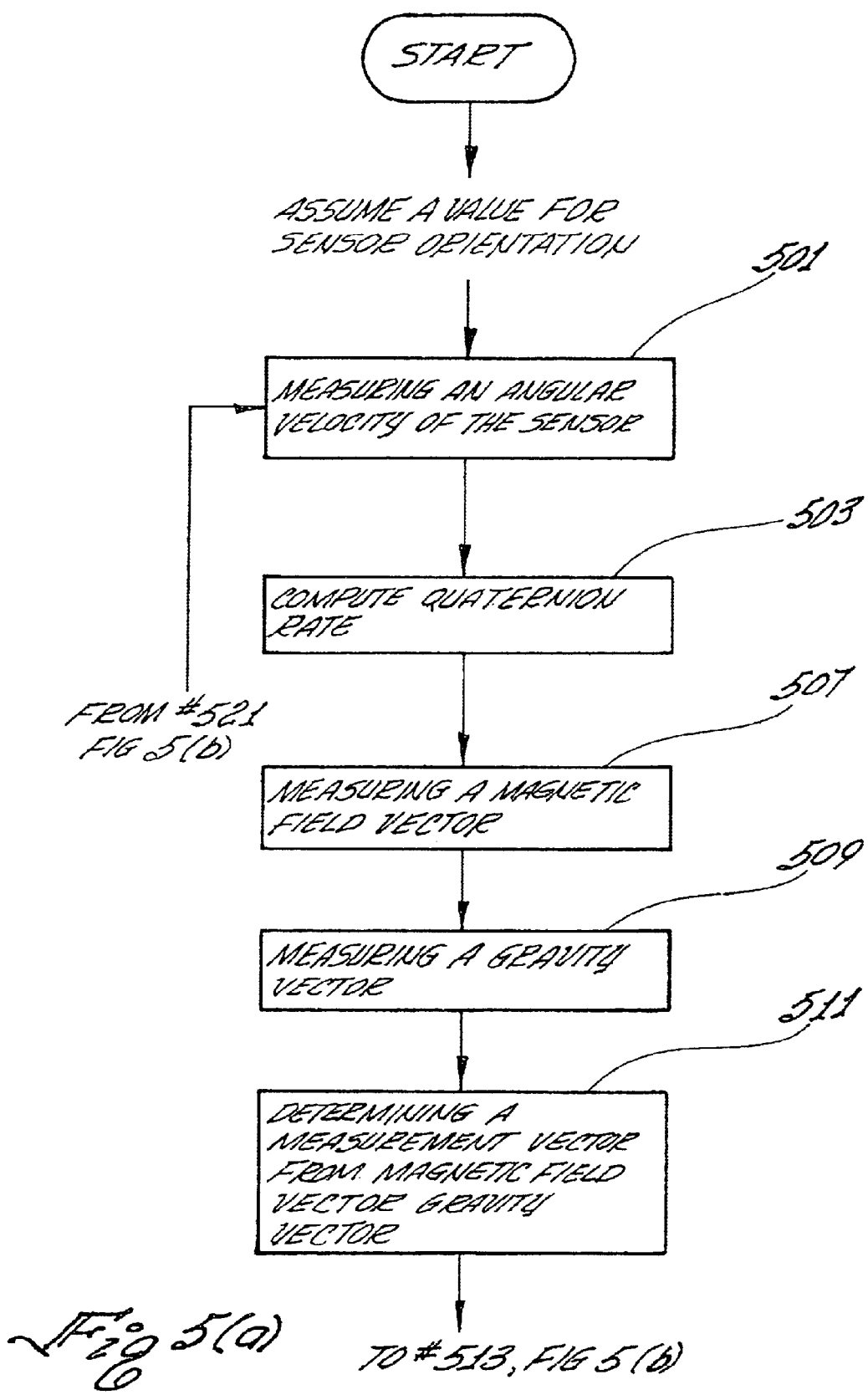
FIGS. 5 and 6 are flow diagrams illustrating method embodiments in accordance with the principles of the present invention.
Figure 5B:
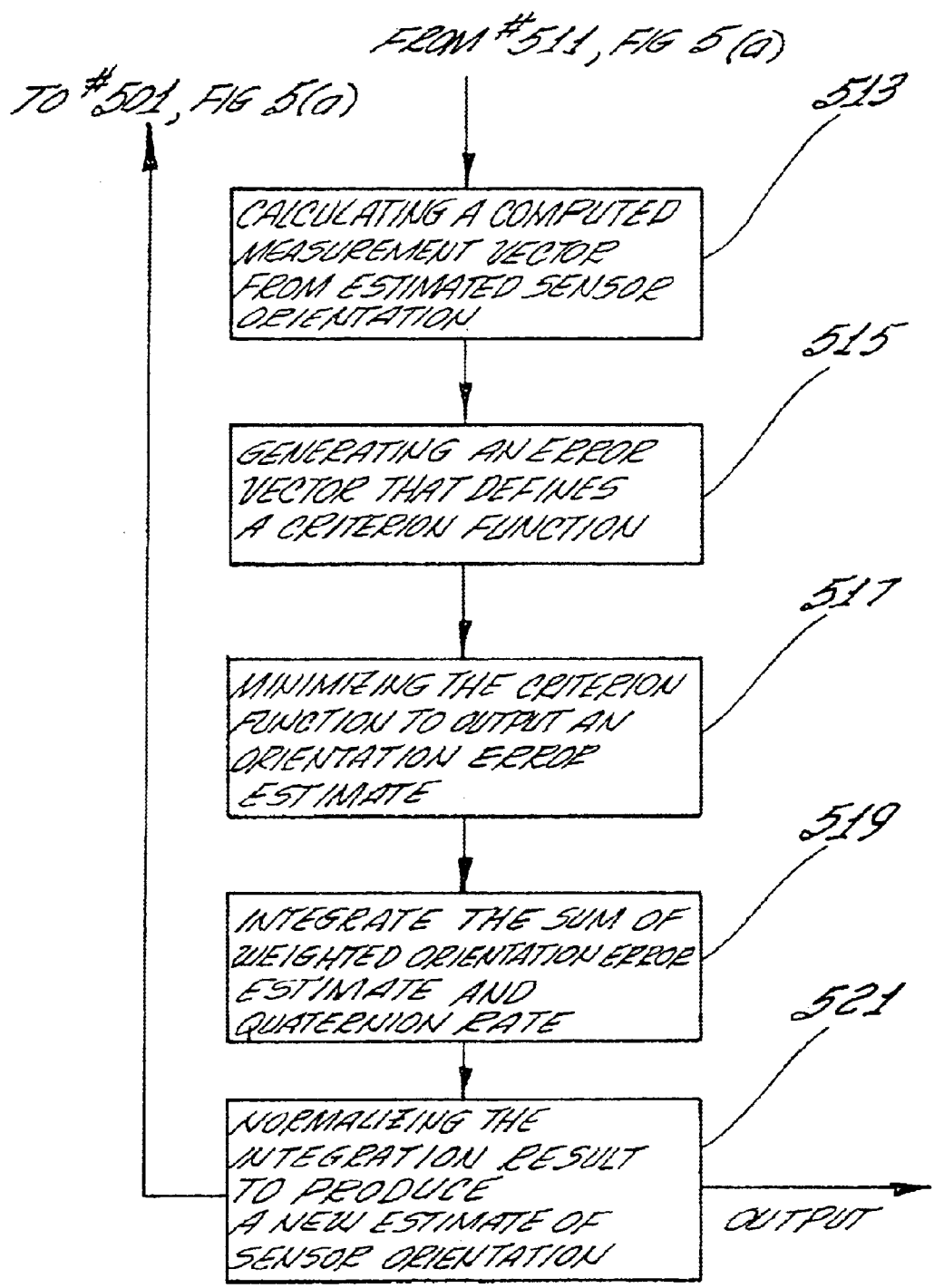
Figure 6A:
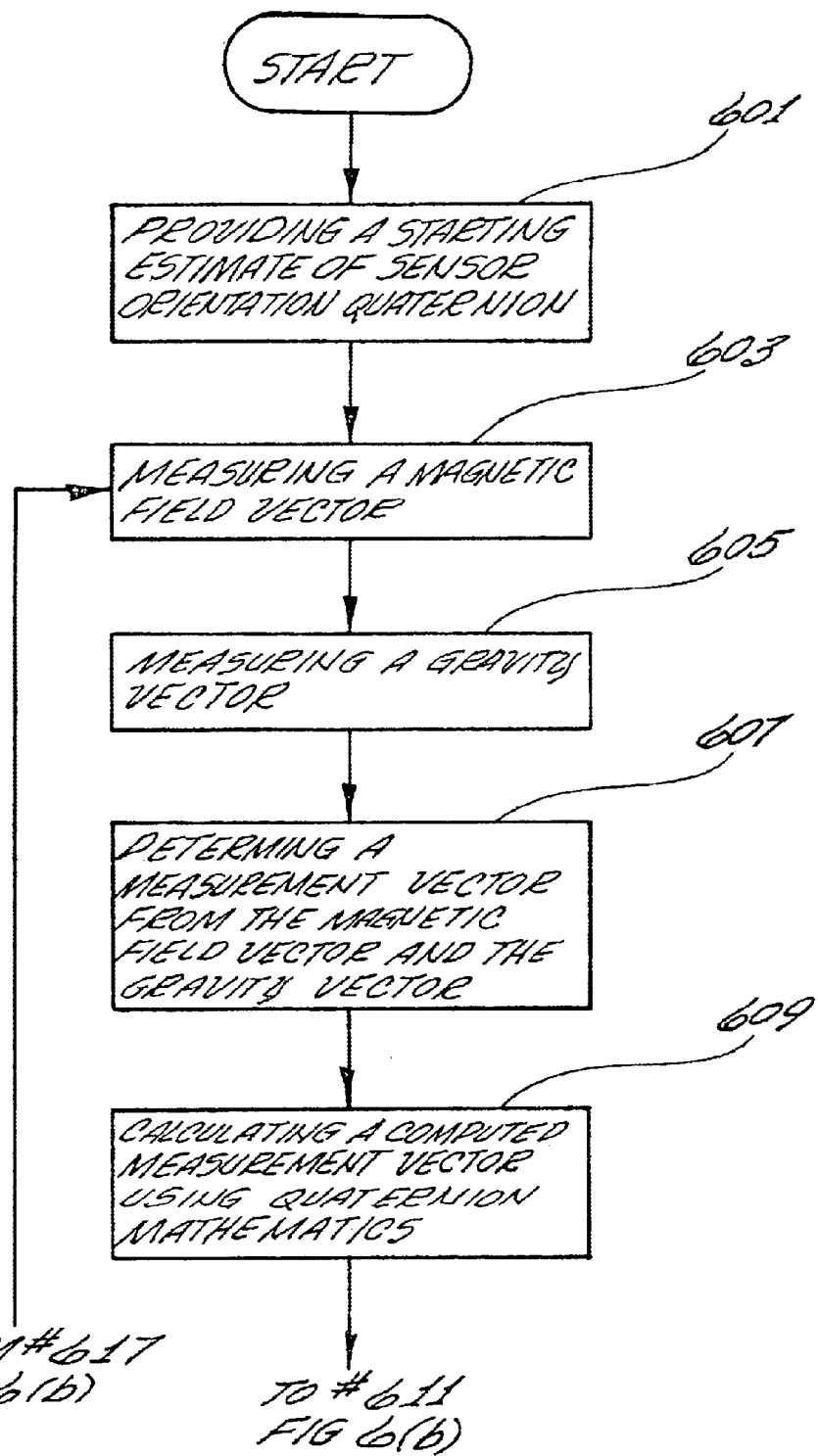
Figure 6B:
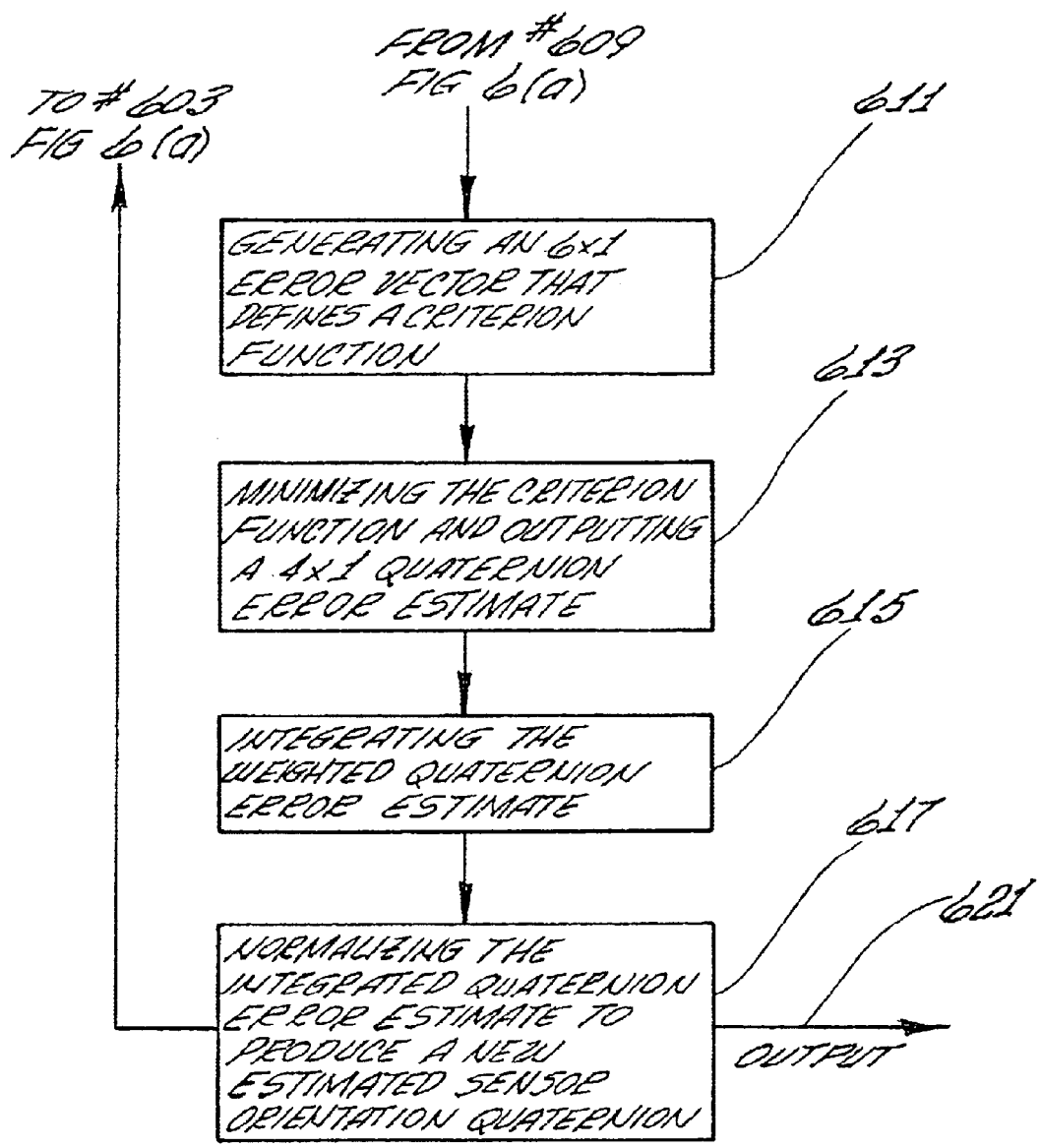

FIGS. 5 and 6 are block diagrams illustrating certain aspects of method embodiments of the present invention. FIG. 5 describes a method embodiment for motion tracking using angular rate detector information complemented with magnetic vector and gravity vector information. The angular rate detector measures an angular velocity of the sensor to generate angular rate values (501). These angular rate values are integrated (503) and normalized (505) to produce an estimate of sensor orientation. A magnetic field vector is measured to generate local magnetic field vector values (507). An acceleration vector is measured to generate local gravity vector values (509). A measurement vector is determined from the local magnetic field vector values and the local gravity vector values (511). A computed measurement vector is calculated from the estimate of sensor orientation (513). The measurement vector is compared with the computed measurement vector to generate an error vector that defines a criterion function (515). A mathematical operation is then performed resulting in the minimization of the criterion function and the generation of an error estimate (517). The error estimate is integrated (519) and normalized (521) to produce a new estimate of sensor orientation (521). In general, these new estimates of sensor orientation are output as sensor orientation signals that can be used to track the orientation of the sensor (525). The operations of (501–525) are repeated using the new estimate of sensor orientation for (513) calculating a computed measurement vector (523). Such process continually outputting sensor orientation information and receiving new detector input to adjust sensor orientation information until tracking is no longer desired. The details of executing each of these operations has been explained hereinabove.

FIG. 6 describes another method embodiment for motion tracking using quaternion mathematics. The method begins by providing a starting estimate of sensor orientation quaternion (601). As previously explained, the starting estimate can be any estimate of sensor orientation including a randomly chosen estimate of sensor orientation. The magnetic field vector and an acceleration vector are measured to generate local magnetic field vector values (603) and local gravity vector values (605). These values are used to determine a measurement vector (607). A computed measurement vector is then calculated from the estimate of sensor orientation using quaternion mathematics (609). The measurement vector is compared with the computed measurement vector to generate a 6×1 error vector that defines a criterion function (611). A mathematical operation is performed that results in the minimization of the criterion function and outputs a 4×1 quaternion error estimate (613). As previously explained, this mathematical operation can using the X matrix, for example, by multiplying $[X^T X]^{-1} X^T$ with the error vector. As is known to persons having ordinary skill in the art other operations can be used. The 4×1 quaternion error estimate is integrated (615) and normalized (617) to produce a new estimated sensor orientation quaternion. This new estimated sensor orientation quaternion can be output as a sensor orientation signal and used for tracking (621). Also, the operations of 601–621 are repeated, wherein the new estimated sensor orientation quaternion is used for calculating (609) a computed measurement vector (619). Such process continually outputting sensor orientation quaternions and receiving new detector input to adjust sensor orientation quaternions until tracking is no longer desired. The details of executing each of these operations has been explained hereinabove.

The present invention has been particularly shown and described with respect to certain preferred embodiments and specific features thereof. However, it should be noted that the above described embodiments are intended to describe the principles of the invention, not limit its scope. Therefore, as is readily apparent to those of ordinary skill in the art, various changes and modifications in form and detail may be made without departing from the spirit and scope of the invention as set forth in the appended claims. Other embodiments and variations to the depicted embodiments will be apparent to those skilled in the art and may be made without departing from the spirit and scope of the invention as defined in the following claims. In particular, it is contemplated by the inventors that the principles of the present invention can be practiced to track the orientation of simple rigid bodies such as weapons or simulated weapons. Additionally, the inventors contemplate tracking the posture of many types of articulated rigid bodies including, but not limited to prosthetic devices, robot arms, moving automated systems, and living bodies. Also, the inventors contemplate other filtering embodiments including, but not limited to Weiner and Kalman filters. Further, reference in the claims to an element in the singular is not intended to mean "one and only one" unless explicitly stated, but rather, "one or more". Furthermore, the embodiments illustratively disclosed herein can be practiced without any element which is not specifically disclosed herein.

We claim:

1. A method of tracking the orientation of a sensor, the method comprising:
   a) measuring an angular velocity of the sensor to generate angular rate values;
   b) integrating the angular rate values;
   c) normalizing the integrated angular rate values to produce an estimate of sensor orientation;
   d) measuring a magnetic field vector to generate local magnetic field vector values;
   e) measuring an acceleration vector to generate local gravity vector values; and
   f) correcting the estimate of sensor orientation using the local magnetic field vector and local gravity vector,
   wherein correcting the estimate of sensor orientation using the local magnetic field vector and local gravity vector comprises:
   g) determining a measurement vector from the local magnetic field vector values and the local gravity vector values;
   h) calculating a computed measurement vector from the estimate of sensor orientation;
   i) comparing the measurement vector with the computed measurement vector to generate an error vector that defines a criterion function;
   j) performing a mathematical operation that results in the minimization of the criterion function and outputs an error estimate;
      wherein the operation of performing a mathematical operation that results in the minimization of the criterion function includes implementing a partial correction step to compensate for measurement error;
      wherein implementing the partial correction step to compensate for measurement error is supplemented by using a weighted least squares regression to emphasize more reliable measurements with respect to less reliable measurements;
   k) integrating the error estimate;
   l) normalizing the integrated error estimate to produce a new estimate of sensor orientation; and
   m) repeating steps a)–m), wherein the new estimate of sensor orientation is used for h), calculating a computed measurement vector until tracking is no longer desired.

2. A method of tracking the orientation of a sensor, the method comprising:
   a) measuring an angular velocity of the sensor to generate an angular rate quaternion;
   b) integrating the angular rate quaternion;
   c) normalizing the integrated angular rate quaternion to produce an estimated sensor orientation quaternion; and
   d) measuring a magnetic field vector to generate local magnetic field vector values;
   e) measuring an acceleration vector to generate local gravity vector values;
   f) correcting the estimated sensor orientation quaternion using the local magnetic field vector and local gravity vector;
   wherein correcting the estimated sensor orientation quaternion using the local magnetic field vector and local gravity vector comprises:
   g) determining a measurement vector from the local magnetic field vector values and the local gravity vector values;
   h) calculating a computed measurement vector from the estimated sensor orientation quaternion;
   i) comparing the measurement vector with the computed measurement vector to generate an error vector that defines a criterion function;
   j) performing a mathematical operation that results in the minimization of the criterion function and outputs an error estimate quaternion;
   wherein the operation of performing a mathematical operation that results in the minimization of the criterion function comprises minimizing the criterion function without calculating the criterion function;
   wherein the operation of performing a mathematical operation that results in the minimization of the criterion function includes implementing a partial correction step to compensate for measurement error;
   wherein implementing the partial correction step to compensate for measurement error is supplemented by using a weighted least squares regression to emphasize more reliable measurements with respect to less reliable measurements;
   k) integrating the error estimate quaternion;
   l) normalizing the integrated error estimate quaternion to produce a new estimated sensor orientation quaternion; and
   m) repeating steps a)–m), wherein the new estimated sensor orientation quaternion is used for h), calculating a computed measurement vector.

3. A method of tracking the orientation of a sensor, the method comprising:
   a) providing a starting estimate of sensor orientation;
   b) measuring a magnetic field vector to generate local magnetic field vector values;
   c) measuring an acceleration vector to generate local gravity vector values;
   d) determining a measurement vector from the local magnetic field vector values and the local gravity vector values;
   e) calculating a computed measurement vector from the estimate of sensor orientation;
   f) comparing the measurement vector with the computed measurement vector to generate an error vector that defines a criterion function;
   g) performing a mathematical operation that results in the minimization of the criterion function and outputs an error estimate;
   wherein the operation of performing a mathematical operation that results in the minimization of the criterion function includes implementing a partial correction step to compensate for measurement error;
   wherein implementing the partial correction step to compensate for measurement error is supplemented by using a weighted least squares regression to emphasize more reliable measurements with respect to less reliable measurements;
   h) integrating the error estimate;
   i) normalizing the integrated error estimate to produce a new estimate of sensor orientation; and j) repeating steps a)–j), wherein the new estimate of sensor orientation is used for e), calculating a computed measurement vector.

4. A method of tracking the orientation of a sensor, the method comprising:
   a) providing a starting estimate of sensor orientation quaternion;
   b) measuring a magnetic field vector to generate local magnetic field vector values;
   c) measuring an acceleration vector to generate local gravity vector values;
   d) determining a measurement vector from the local magnetic field vector values and the local gravity vector values;
   e) calculating a computed measurement vector from the estimate of sensor orientation, using quaternion mathematics;
   f) comparing the measurement vector with the computed measurement vector to generate an 6×1 error vector that defines a criterion function;
   g) performing a mathematical operation that results in the minimization of the criterion function and outputs a 4×1 quaternion error estimate;
   wherein the operation of g), performing a mathematical operation that results in the minimization of the criterion function and outputs a 4×1 quaternion error estimate further includes implementing a partial correction step to compensate for measurement error;
   wherein implementing the partial correction step to compensate for measurement error is supplemented by using a weighted least squares regression to emphasize more reliable measurements with respect to less reliable measurements;
   h) integrating the quaternion error estimate;
   i) normalizing the integrated quaternion error estimate to produce a new estimated sensor orientation quaternion; and
   j) repeating steps a)–j), wherein the new estimated sensor orientation quaternion is used for e), calculating a computed measurement vector.

5. A method of tracking the orientation of a sensor, the method comprising:
   a) measuring a magnetic field vector to generate local magnetic field vector values;
   b) measuring an acceleration vector to generate local gravity vector values;
   c) determining a measurement vector from the local magnetic field vector values and the local gravity vector values;
   d) calculating a computed measurement vector from the estimate of sensor orientation
   e) comparing the measurement vector with the computed measurement vector to generate an error vector that defines a criterion function; and
   f) performing a mathematical operation that results in the minimization of the criterion function using reduced order Gauss-Newton iteration.

6. A method of tracking as in claim 5 wherein the reduced order Gauss-Newton iteration takes into account that there are only three independent elements in a quaternion.

7. A method of tracking as in claim 5 wherein the reduced order Gauss-Newton iteration requires the inversion of a matrix with a dimensionality of no more than 3×3.

8. A method of tracking as in claim 5 wherein the reduced order Gauss-Newton iteration utilizes a reduced order 6×3 matrix entirely composed of elements of the computed measurement vector.

\* \* \* \* \*